US012697159B2

(12) United States Patent
Brojek

(10) Patent No.: US 12,697,159 B2
(45) Date of Patent: Aug. 4, 2026

(54) SURGICAL CRYOPROBE FOR TREATING CRYOLESIONS IN THE SACROILIAC JOINT AREA

(71) Applicant: Metrum Cryoflex Sp. z. o. o., Sp. k., Łomianki (PL)

(72) Inventor: Wiesław Brojek, Janów (PL)

(73) Assignee: METRUM CRYOFLEX S.A., Stare Babice (PL)

( * ) Notice: Subject to any disclaimer, the term of this patent is extended or adjusted under 35 U.S.C. 154(b) by 545 days.

(21) Appl. No.: 18/066,122

(22) Filed: Dec. 14, 2022

(65) Prior Publication Data

US 2023/0181232 A1     Jun. 15, 2023

Related U.S. Application Data

(60) Provisional application No. 63/265,377, filed on Dec. 14, 2021.

(51) Int. Cl.
     *A61B 18/02*          (2006.01)
(52) U.S. Cl.
     CPC .. *A61B 18/0218* (2013.01); *A61B 2018/0212* (2013.01)
(58) Field of Classification Search
     CPC ................ A61B 18/0218; A61B 18/02; A61B 2018/0212; A61B 2018/0268; A61B 2018/0262; A61B 2018/0293
     See application file for complete search history.

(56) References Cited

U.S. PATENT DOCUMENTS

| | | |
|---|---|---|
| 6,505,629 B1 | 1/2003 | Mikus et al. |
| 8,298,220 B2 | 10/2012 | Devens, Jr. et al. |
| 8,740,891 B2 | 6/2014 | Babkin et al. |

(Continued)

FOREIGN PATENT DOCUMENTS

| | | |
|---|---|---|
| EP | 2683315 B1 | 10/2016 |
| WO | 2006034295 A2 | 3/2006 |

(Continued)

OTHER PUBLICATIONS

International Search Report for PCT Application No. PCT/IB2022/062253 dated Mar. 20, 2023. The International Bureau of WIPO.

(Continued)

*Primary Examiner* — Niketa Patel
*Assistant Examiner* — Joshua Brendon Solomon
(74) *Attorney, Agent, or Firm* — WALKER & JOCKE

(57)          ABSTRACT

An apparatus for performing cryosurgery, especially suited for the sacroiliac joint. The apparatus includes a first expansion tube having a first length; a second expansion tube having a second length, wherein the second length is longer than the first length; a first supply tube supplying a cooling agent to the first expansion tube; a second supply tube supplying another cooling agent to the second expansion tube; and a drain tube for removing cooling agents from an enclosed working part, wherein the first expansion tube supplies the cooling agent to a first portion of the working part, the second expansion tube supplies the another cooling agent to a second portion of the working part, the working part further including a tip; wherein the first expansion tube and the second expansion tube are positioned inside a casing.

7 Claims, 25 Drawing Sheets

(56)                    References Cited

U.S. PATENT DOCUMENTS

| | | | |
|---|---|---|---|
| 2008/0051776 A1 | 2/2008 | Bliweis et al. | |
| 2012/0130364 A1* | 5/2012 | Besch ...................... | A61N 1/06 |
| | | | 606/33 |
| 2014/0276700 A1* | 9/2014 | McKay .................. | A61B 18/02 |
| | | | 606/21 |
| 2017/0311789 A1* | 11/2017 | Mulcahey .............. | A61B 1/126 |
| 2020/0060942 A1* | 2/2020 | Rajagopalan ........ | A61B 5/6852 |
| 2020/0085485 A1* | 3/2020 | Skorich .................. | A61B 18/02 |

FOREIGN PATENT DOCUMENTS

| | | | |
|---|---|---|---|
| WO | 2015057450 A1 | 4/2015 | |
| WO | 2016183337 A2 | 11/2016 | |
| WO | 2020056221 A1 | 3/2020 | |

OTHER PUBLICATIONS

Written Opinion of the International Searching Authority for PCT Application No. PCT/IB2022/062253 dated Mar. 20, 2023. The International Bureau of WIPO.

\* cited by examiner

SURGICAL CRYOPROBE FOR TREATING CRYOLESIONS IN THE SACROILIAC JOINT AREA

CROSS-REFERENCE TO RELATED APPLICATIONS

This application claims the benefit of U.S. Provisional Application No. 63/265,377 filed on Dec. 14, 2021, the contents of which are hereby incorporated by reference.

All of the applications referenced above are hereby incorporated by reference.

TECHNICAL FIELD

The present disclosure relates generally to cryoprobe surgical instruments, and specifically to cryoprobes for treating the sacroiliac joint.

BACKGROUND

The sacroiliac joint in humans is where the pelvis meets the spine. It is a flat joint, formed by the sacrum and ilium, with little mobility. The sacrum is a large bone at the base of the spine, composed of 5 fused vertebrae.

The functions of the sacroiliac joint include supporting the weight of the torso and upper limbs, and cushioning the shocks transmitted from the pelvis to the spine while moving.

The sacroiliac joint is the largest nerve plexus in the human body, the so-called sacroiliac weave. It supplies the vast majority of the lower limb, pelvic organs, perineum, external genitalia, skin, and the coccyx muscles.

A widespread method of treating pain in the lower spine is a pharmacological regiment, based on painkillers, many containing opioids, which, with long-term use, are known to have destructive effects, such as on the digestive system and metabolism and lead to concentration disorders. Opioids are also known to lead to what is referred to as a closed circle of pain, with addiction to increasing doses of opiates.

Another method of treating lower back pain symptoms is the use of blockages, i.e. an injection into the sacroiliac joint to combat degenerative conditions, where the administration of the fluid may result in absorption, not necessarily at the intended site.

There are also known solutions that destroy the sacroiliac joint nerves, by high temperature, known as thermolesion, which irreversibly destroys nerves. This can be performed on a single nerve such as described in U.S. Patent Publication 2021/177502 A1, or on several nerves simultaneously, such as described in U.S. Patent Publication 2007/055316 A1.

In minimally invasive pain therapy, solutions related to surgical cryoprobes acting on single nerve endings are known and widely used. Known surgical cryoprobes operate on the principle of the Joule-Thompson effect, describing the change in temperature of the real gas during the isenthalpic expansion of the gas through the septum (throttling) from an area of higher pressure to an area of lower pressure. Using this dependence, the pressurized cooling medium under high pressure is expanded through the nozzle inside the cylindrical tool. Expansion cools the steel shell very quickly, creating an icy space around the tool.

Typical embodiments of surgical cryoprobes usually include a single heat exchange system that induces heat exchange between the inlet tube and the outlet tube, aligned and centered inside a cylindrical housing, with the distal end of the outlet tube acting as an expansion nozzle and being the farthest element within the probe structure.

Known surgical cryoprobes consist of a casing covering the supply and drain ducts/tubes, and a freezing tip that is applied to the patient's tissue. The tip can be of different size and shape, depending on the target.

WO2006034295 discloses a surgical cryoprobe for oncological use, comprising an electrically conductive first part and two cooling elements in the form of two heat exchangers for enlarging the freezing zone. The removable housing has an electrically conductive second part spaced from the electrically conductive first part of the probe. Electrical insulation is provided between the first part and the second part. In operation, the cooling elements cool the tissue around the probe part, while the electromagnetic energy moving between the first part and the second part heats the tissue adjacent to the cooled tissue. Cooling alters the path of electromagnetic energy by changing the electrical conductivity of the tissue in the area of action of the cryoprobe. In addition, the probe according to the examples given uses Argon as a cooling agent. This solution, used mainly in oncological procedures, is characterized by a complex structure and large dimensions.

It would therefore be advantageous to provide a solution for treating the sacroiliac joint, that would overcome at least some of the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include an apparatus for cryosurgery. The apparatus comprises: a first expansion tube having a first length; a second expansion tube having a second length, wherein the second length is longer than the first length; a first supply tube supplying a cooling agent to the first expansion tube; a second supply tube supplying another cooling agent to the second expansion tube; and a drain tube for removing cooling agents from an enclosed working part, wherein the first expansion tube supplies the cooling agent to a first portion of the working part, the second expansion tube supplies the another cooling agent to a second portion of the working part, the working part further including a tip; wherein the first expansion tube and the second expansion tube are positioned inside a casing.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
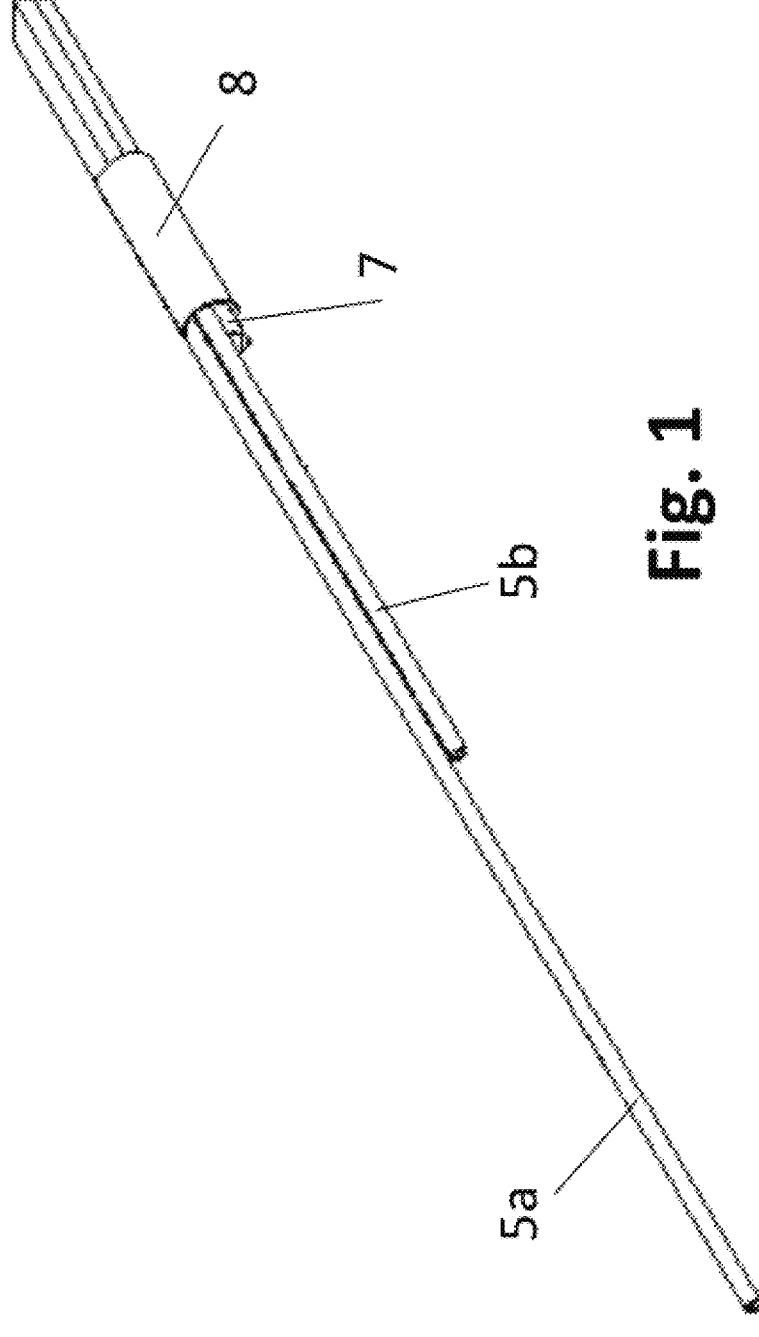
FIG. 1 is an axonometric view of the probe flow assembly.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

According to an embodiment, a surgical cryoprobe includes a first expansion tube having a first length, a second expansion tube having a second length, wherein the second length is longer than the first length, a first supply tube supplying a cooling agent to the first expansion tube, a second supply tube supplying another cooling agent to the second expansion tube, and a drain tube for removing cooling agents from a working part, wherein the first expansion tube supplies the cooling agent to a first portion of the working part, the second expansion tube supplies the another cooling agent to a second portion of the working part, the working part further including a tip. The first expansion tube and the second expansion tube are positioned inside a casing, in accordance with an embodiment.

In an embodiment, a surgical cryoprobe disclosed herein is manufactured to perform cryolesion therapy in the area of the sacroiliac joint, to which the sensory branches of the sacroiliac nerve connect, passing through small diameter holes in the sacrum. Utilizing such a cryoprobe allows, in an embodiment, to perform a small direct puncture or a small incision of skin, which traumatizes the patient as little as possible. Another advantage of a disclosed embodiment is a cryoprobe manufactured to generate an even zone of ice, which is able to cover nerves, tissue, combination thereof, and the like. For example, in an embodiment where freezing nerves in the sacroiliac joint area is desired, it is advantageous to manufacture a probe with a shape (e.g., profile) which is configured to adhere to the sacrum.

Figure 2:
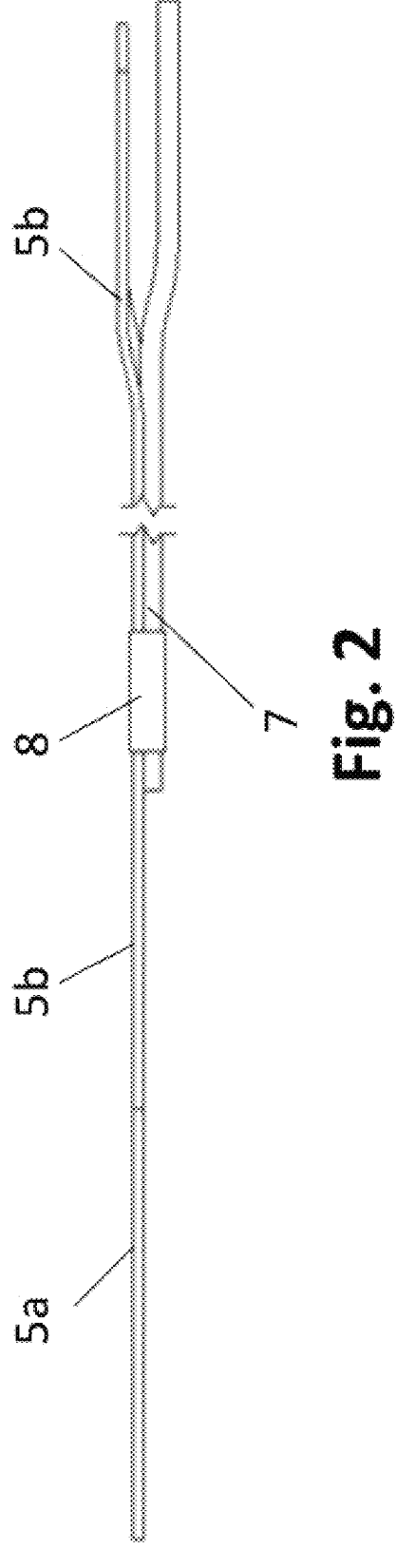
FIG. 2 is a sectional side view of the probe flow assembly.
Figure 3:
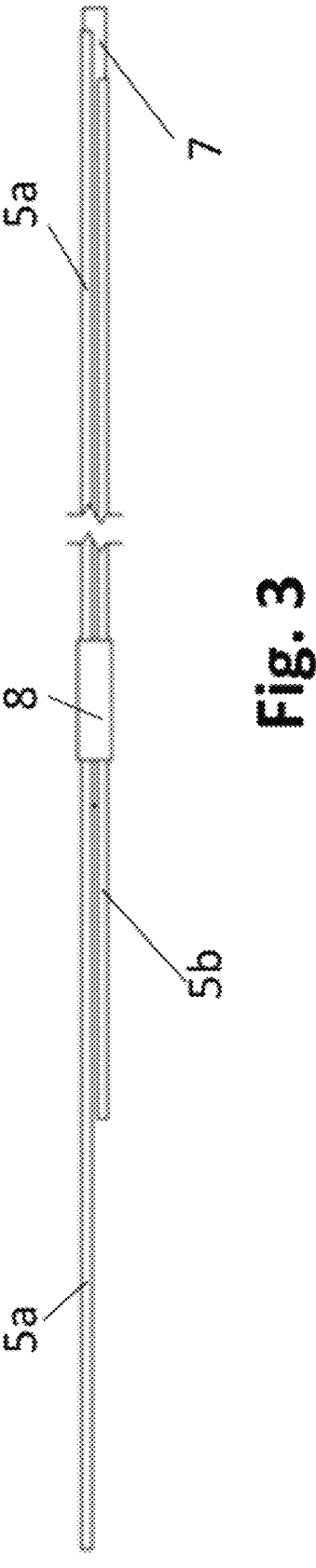
FIG. 3 is a cross-sectional view of the probe flow assembly in a top view.
Figure 4:
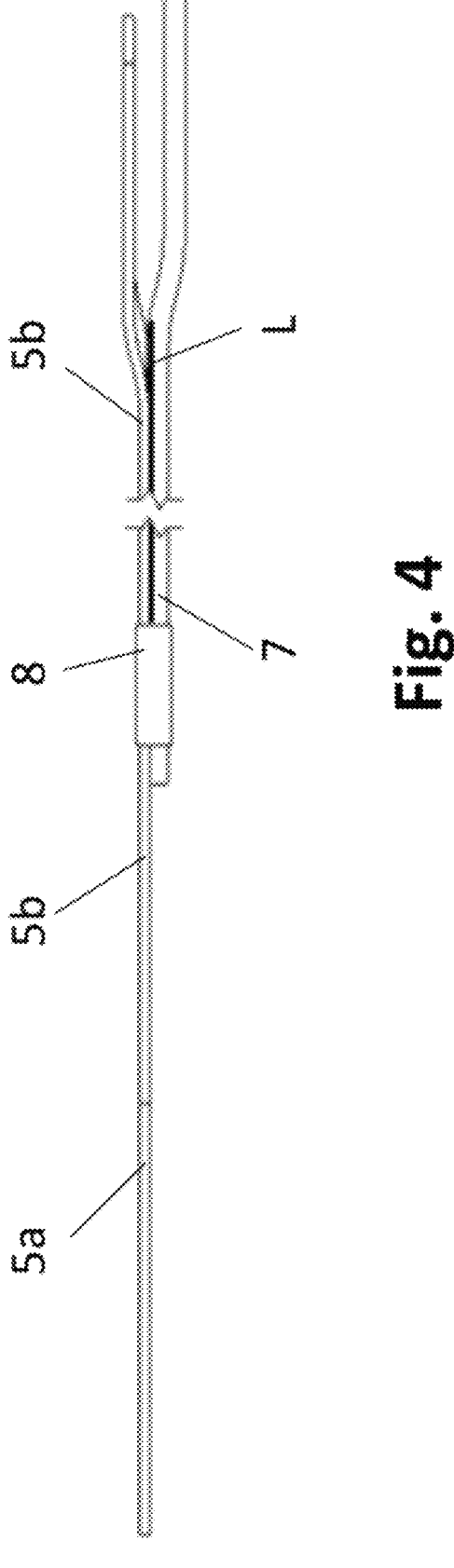
FIG. 4 is a sectional side view of the probe flow assembly, with expansion tubes and a drain tube shown connected between the handle and the expansion chamber by soldering.
Figure 5:
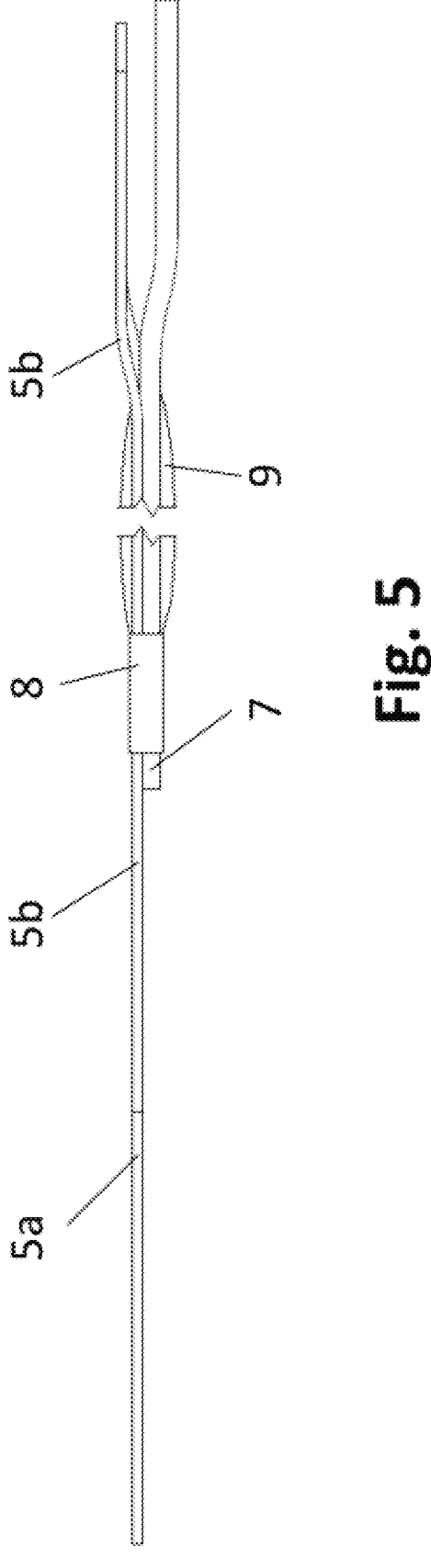
FIG. 5 is a sectional side view of the probe flow assembly with expansion tubes and a drain tube shown with an insulating casing applied thereon.
Figure 6:
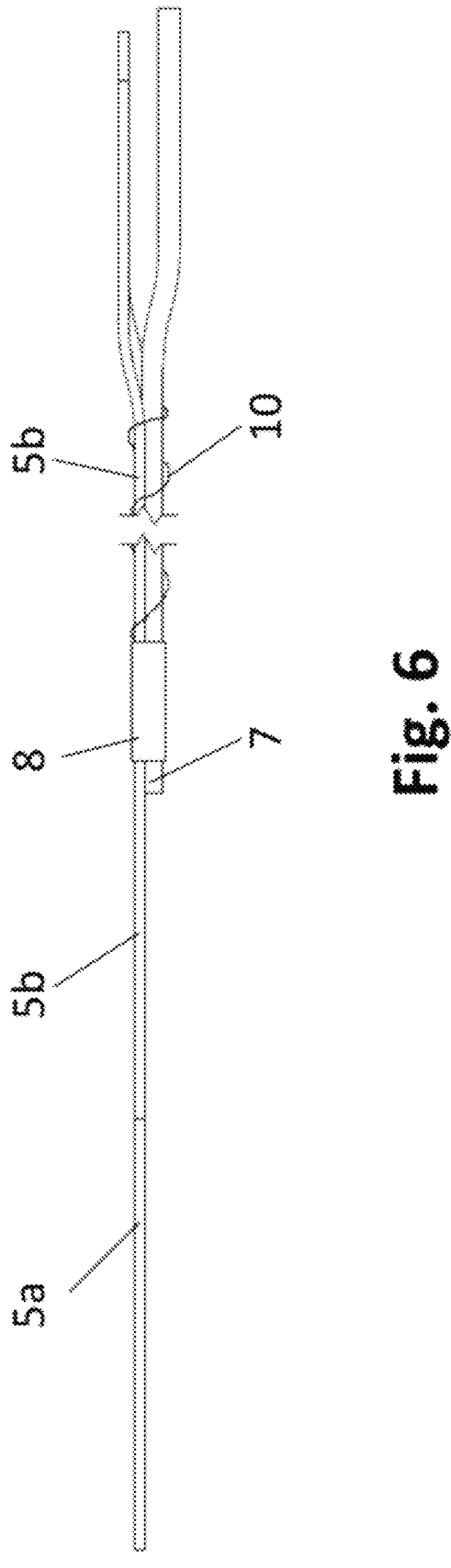
FIG. 6 is a sectional side view of the probe flow assembly, with expansion tubes and a drain tube wrapped with a thread or wire of insulating material.

Reference is now made to FIGS. 1 through 6. FIG. 1 is an example of an axonometric view of a cryoprobe flow assembly, implemented according to an embodiment. FIG. 2 is an example of a sectional side view of the cryoprobe flow assembly, implemented in accordance with an embodiment. FIG. 3 is an example of a cross-sectional top view of the cryoprobe flow assembly, implemented according to an embodiment. FIG. 4 is an example of a sectional side view of the cryoprobe flow assembly, with expansion tubes and a drain tube connected by soldering between a handle and an expansion chamber, implemented in accordance with an embodiment. FIG. 5 is an example of a sectional side view of the cryoprobe flow assembly with expansion tubes and a drain tube with an insulating casing applied thereon, implemented according to an embodiment. FIG. 6 is an example of a sectional side view of the cryoprobe flow assembly, with expansion tubes and a drain tube wrapped with an insulator.

The flow assembly includes, according to an embodiment, a flow unit which includes a first expansion tube 5a and a second expansion tube 5b. In some embodiments the flow unit includes a plurality of expansion tubes. In certain embodiments, the first expansion tube 5a has a first length, which is different from a second length of the second expansion tube 5b. Each expansion tube is configured to allow a cooling agent to flow therethrough. In an embodiment, expansion of a cooling agent (such as $CO_2$ or $N_2O$ gases), occurs in several areas, equal to a number of nozzles (i.e., where an expansion tube expels the cooling agent). In certain embodiments the plurality of nozzles is dispersed along the length of the probe tip. In some embodiments, the first expansion tube 5a includes a first cooling agent (e.g., $CO_2$), and the second expansion tube 5b includes a second cooling agent (e.g., $N_2O$).

In an embodiment, the flow unit further includes a drain tube 7. According to an embodiment, the drain tube 7 is attached to the first expansion tube 5a and the second expansion tube 5b with a sleeve 8.

In an embodiment, the sleeve 8 is manufactured by wrapping the first expansion tube 5a, the second expansion tube 5b, and the drain tube 7, with a length of copper wire which is soldered with silver solder, for example to a diameter of 5 mm, resulting in a joint.

The joint is machined, for example on a lathe, according to an embodiment, to obtain a smooth and even outer surface in the form of a sleeve 8, with the first expansion tube 5a and the second expansion tube 5b fixed therein, and further with the drain tube 7. In an embodiment, the first expansion tube 5a, he second expansion tube 5b, and the drain tube 7, are connected along a joint of length "L". In certain embodiments, the connection (i.e., the joint), increases heat transfer from the expansion chamber upon the return of the cooling agent from the expansion chamber to the drain tube 7.

In an embodiment, an insulator 10 is wrapped around the first expansion tube 5a, the second expansion tube 5b, and the drain tube 7. The insulator 10 thermally insulates from an inner surface of a casing 3 (shown in FIG. 7), at least a portion of the flow assembly including the first expansion tube 5a, the second expansion tube 5b, and the drain tube 7. In an embodiment, the insulator 10 is, for example, a wire, a thread, and the like, such as a carbon thread.

In certain embodiments isolating the flow assembly from a casing is performed by applying an insulating sleeve 9. According to an embodiment, the insulating sleeve 9 covers a section of the first expansion tube 5a, the second expansion tube 5b, and the drain pipe 7. In an embodiment, the insulating sleeve 9 is a thermally insulating heat-shrinkable jacket. Upon applying heat to the area, the jacket shrinks in diameter, after which the flow assembly is inserted into an appropriate depth into the casing 3.

Figure 7:
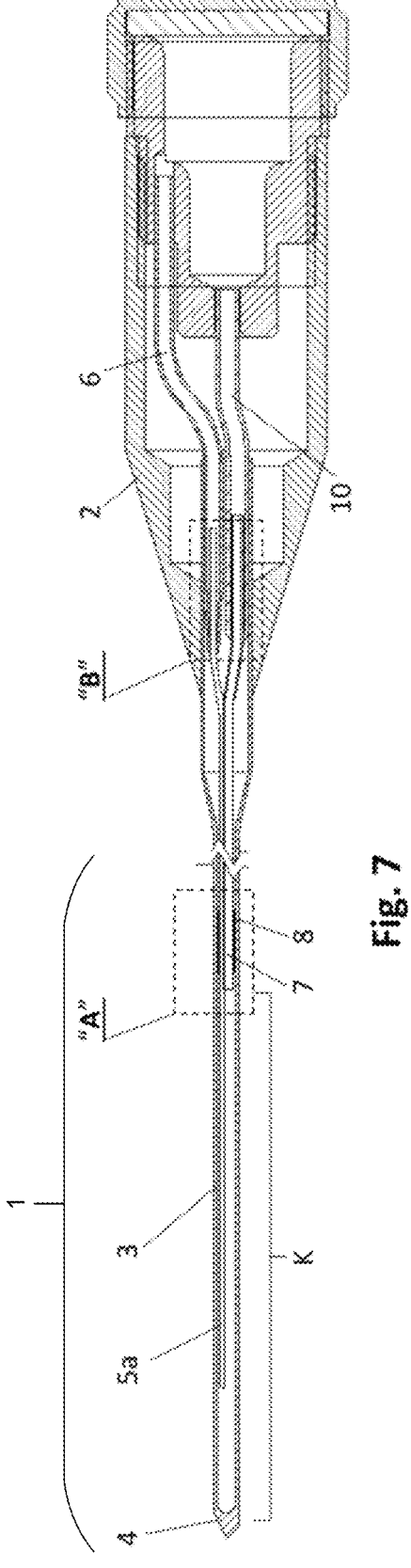
FIG. 7 is a side section of the probe with the marked fragments "A" and "B" of the probe.
Figure 8:
FIG. 8 shows the marked fragment "A" of the probe.
Figure 9:
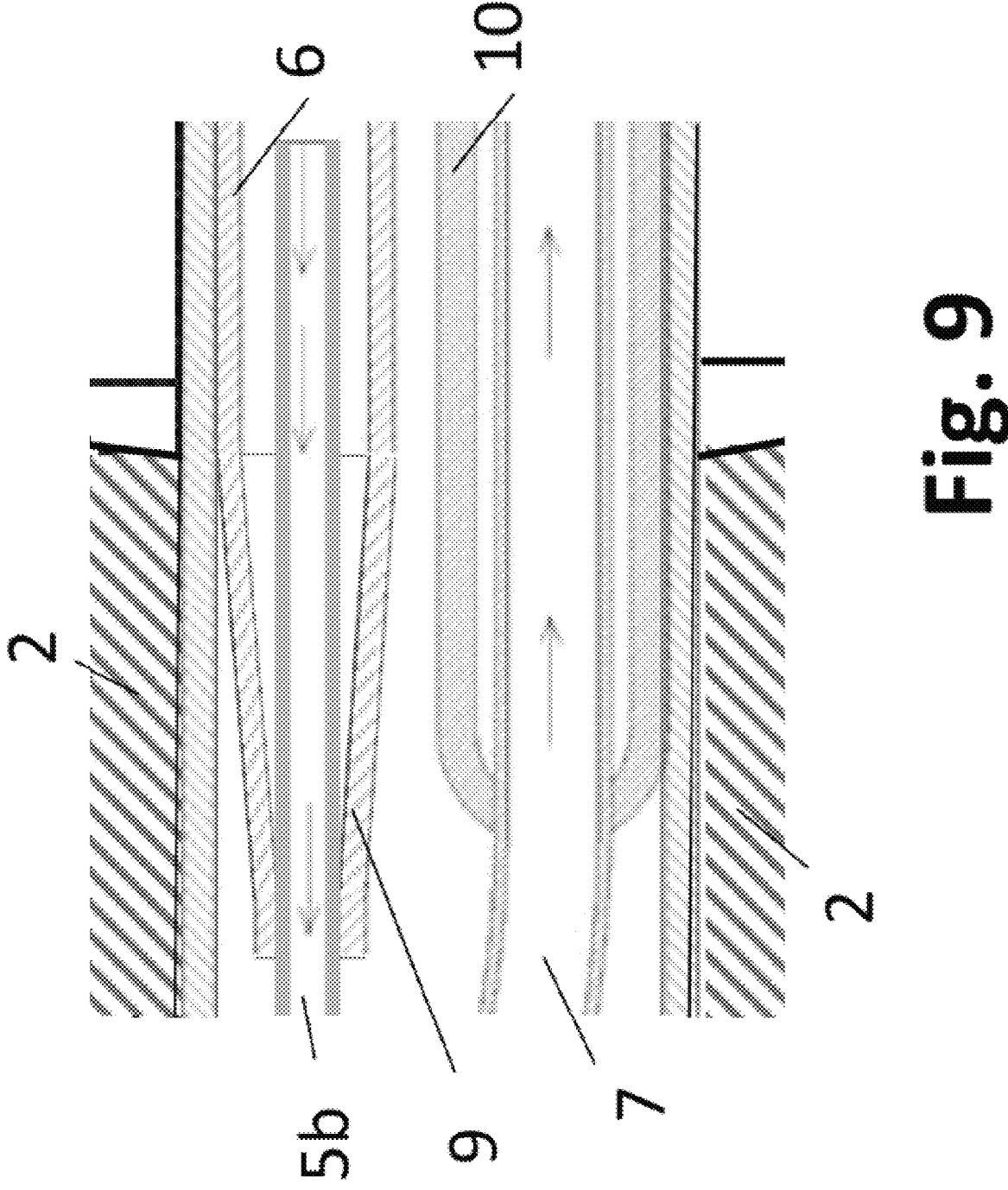
FIG. 9 shows the marked fragment "B" of the probe.

Reference is now made to FIGS. 7 through 9. FIG. 7 is an example of a side section of the cryoprobe with marked segments "A" and "B, utilized to describe an embodiment. FIG. 8 is an example of a diagram of the marked section "A" of the cryoprobe, implemented according to an embodiment. FIG. 9 is an example diagram of the marked section "B" of the cryoprobe, implemented in accordance with an embodiment.

In an embodiment a surgical cryoprobe, for cryolesion therapy in the area of the sacroiliac joint, is implemented as an elongated tool. The surgical cryoprobe has a circular cross-section, discussed in more detail herein. In an embodiment the cryoprobe includes a working part 1 and a second part equipped with a connection to a supply of a cooling medium, and a connection to an outlet of the cooling medium, located in a holder 2. In an embodiment, the working part 1 is a tube, tubular structure, and the like, which is closed on one end, and connected to a handle on a second end. The working part 1 forms an enclosed (an enclosed working part) in which a plurality of expansion tubes are positioned.

According to an embodiment, a supply tube 6 feeds directly into the first expansion tube 5a, the second expansion tube 5b, and a combination thereof. In an embodiment, the first expansion tube 5a and the second expansion tube 5b are connected to the supply tube 6 via a flattened end 11. In an embodiment the connection is manufactured by soldering, for example with silver solder.

In an embodiment, each of the expansion tubes 5a and 5b is supplied by a common supply tube 6. In certain embodiments a plurality of expansion tubes may be utilized, for example, at least one of the first expansion tube 5a, at least one of the second expansion tube 5b, a combination thereof, and the like.

In certain embodiments, the working part 1 includes a casing 3, and an ending having a tip 4. In an embodiment the flow unit is located inside the working part 1. In an embodiment, the casing 3 is made of stainless steel, allowing the cryoprobe to conduct neurostimulation impulses, enabling the localization of correct nerves, and thus avoiding accidental anesthesia of motorial nerves.

In an embodiment an expansion chamber "K" is defined by a space between the tip 4 and the sleeve 8. Outlet openings of the first expansion tube 5a and the second expansion tube 5b are located in the expansion chamber "K" such that the outlet opening of the first expansion tube 5a is nearer to the tip 4, relative to the outlet opening of the second expansion tube 5b. In an embodiment the outlet opening of the expansion tube 5b is located nearer to the sleeve 8, relative to the outlet opening of the first expansion tube 5a.

In some embodiments, such an arrangement of the first expansion tube 5a and the second expansion tube 5b is advantageous, and constitutes a freezing zone of the cryoprobe, along the length of the expansion chamber on the outer part of the casing 3.

In an embodiment, an end of the working part 1 which is closer to the handle 2 includes a drain pipe 7 which extends into the handle 2. A supply pipe 6 further extends into the handle 2, according to an embodiment.

In an embodiment, the sleeve 8, which connects the first expansion tube 5a and the second expansion tube 5b to the drain pipe 7, is press-fitted into the casing 3.

In certain embodiments, an adhesive (not shown) is used in order to form a connecting bond between the sleeve 8 and the casing 3. The adhesive has a fluid consistency, allowing flow on the sleeve surface, according to an embodiment. The adhesive has a high temperature resistance, both at low temperatures during tool operation, and at high temperatures, according to some embodiments. The adhesive is applied, in an embodiment, to the first expansion tube 5a, the second expansion tube 5b, and the drain pipe 7 in a section therebetween, connecting them (i.e., the flow assembly) to the sleeve 8 and the inlet opening of the drain pipe 7. In such an embodiment, a sleeve 8 of shorter length is used, as the sleeve 8 provides support which is made partially redundant by the adhesive.

Figure 10:
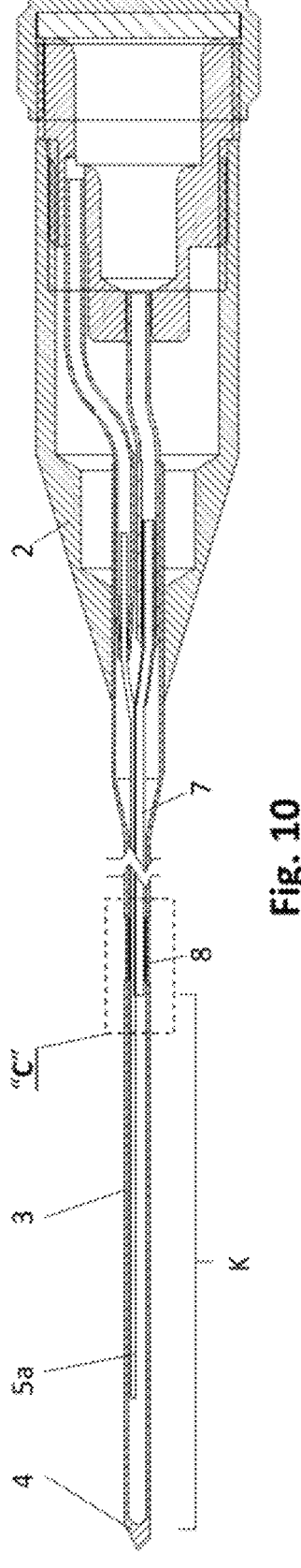
FIG. 10 shows the probe in a cross-section from the side, with the clamped casing at the location of the sleeve, with the fragment "C" of the probe marked.
Figure 11:
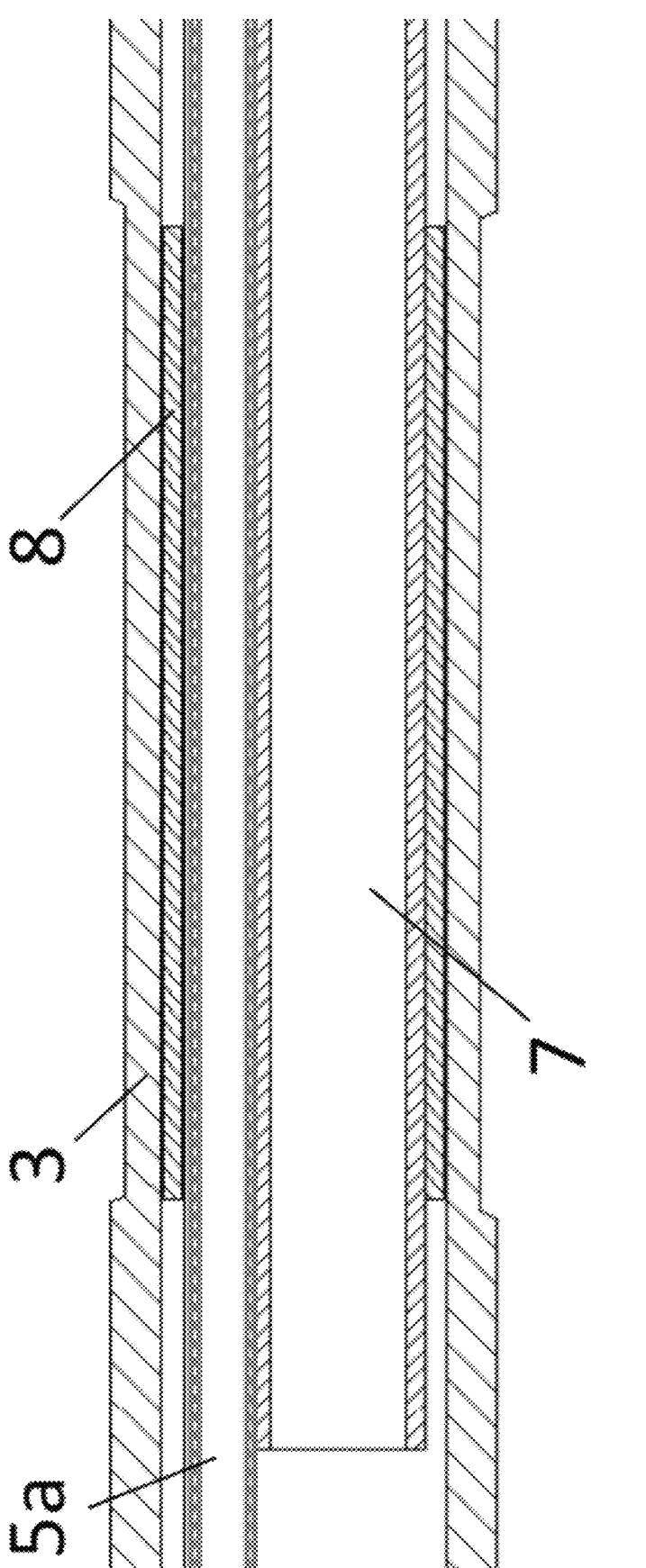
FIG. 11 shows the marked fragment "C" of the probe.

Reference is now made to FIGS. 10 and 11. FIG. 10 is an example of a side cross-section of a cryoprobe, with a clamped casing at the location of the sleeve, with section "C" of the cryoprobe marked, utilized to describe an embodiment. FIG. 11 is an example diagram of the section "C" of the cryoprobe.

In an embodiment, a sleeve 8 is inserted within the casing 3. According to an embodiment, the first expansion tube 5a and second expansion tube 5b are fastened to the sleeve 8, and are inserted, together with the drain pipe 7, into the casing 3. In certain embodiments insertion is performed to a predetermined suitable depth.

In an embodiment, the casing 3 is clamped in place where the sleeve 8 is located. Clamping is performed, according to an embodiment, for example, with rollers, which fix the sleeve 8 in place. In an embodiment this is advantageous as it allows ensuring that the expansion chamber is sealed properly (see, e.g., expansion chamber "X" of FIG. 12 below).

In an embodiment manufacturing the sleeve 8, which connects the set of expansion tubes 5a and 5b and the drain pipe 7, from copper and silver solder, the sleeve 8 is plasticized which is advantageous, as this allows the sleeve to form a strong connection to the inner surface of the casing 3, due to a lower hardness than the stainless steel casing 3.

Figure 12:
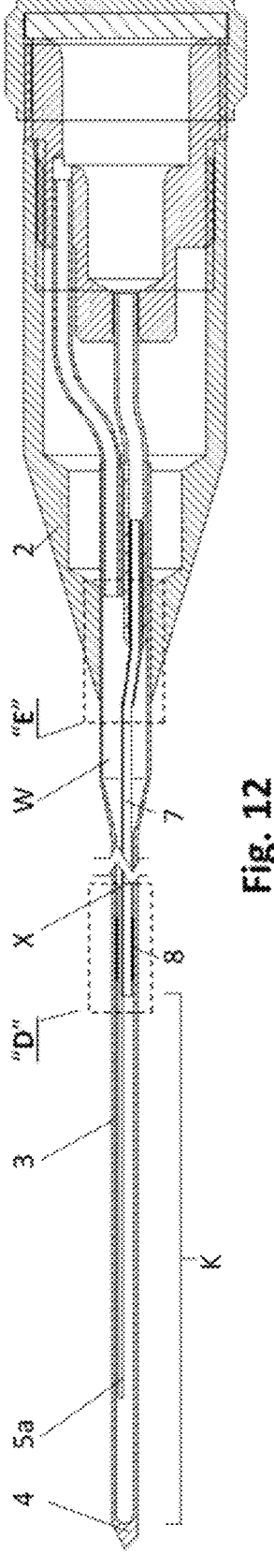
FIG. 12 is a side section view of the probe in an embodiment of the invention with the fragments "D" and "E" of the probe marked.
Figure 13:
FIG. 13 shows the marked fragment "D" of the probe.
Figure 14:
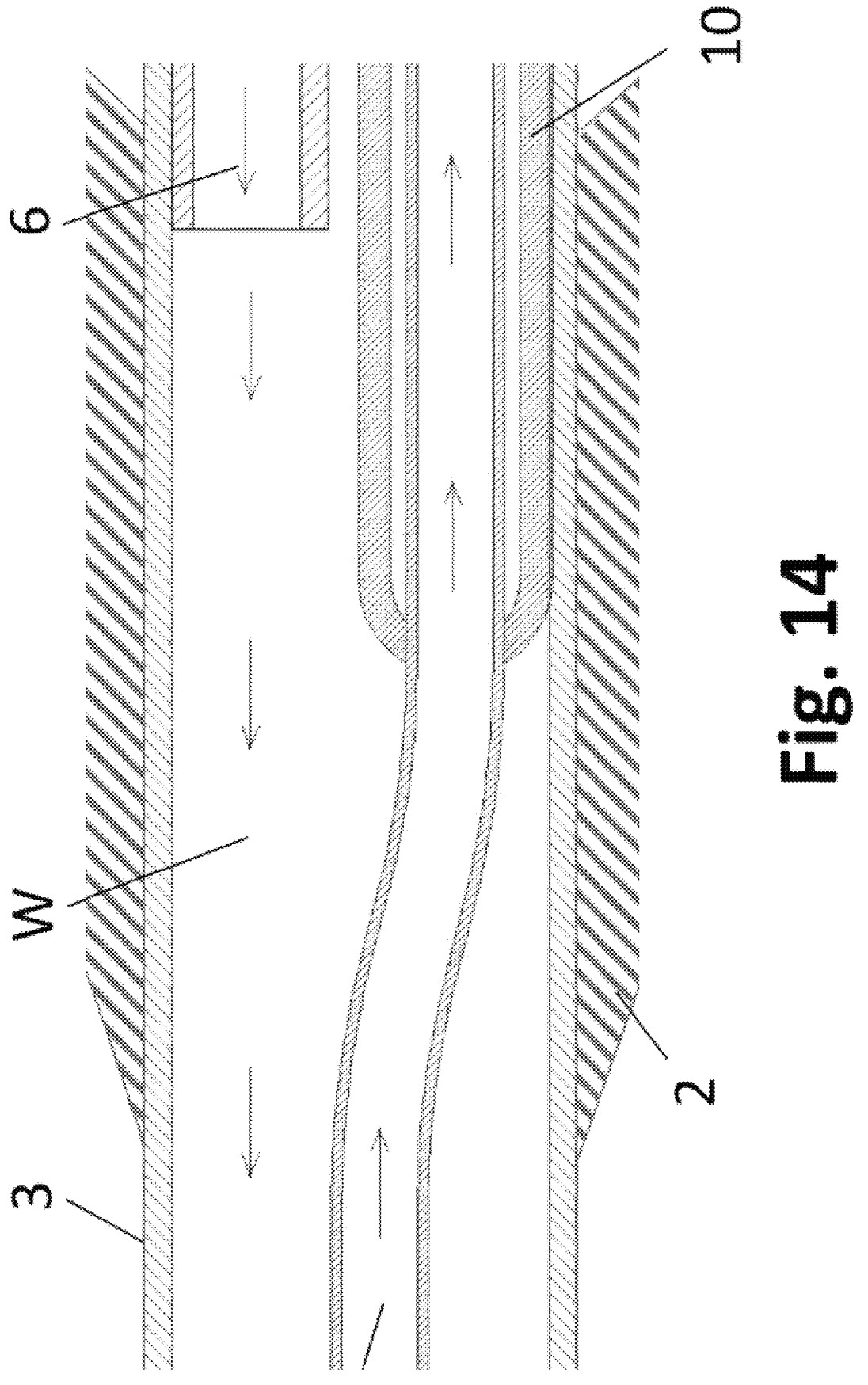
FIG. 14 shows the marked fragment "E" of the probe.

Reference is now made to FIGS. 12 through 14. FIG. 12 is an example of a side section view of a cryoprobe with sections "D" and "E" of the cryoprobe marked, implemented according to an embodiment. FIG. 13 is an example diagram of the section "D" of the cryoprobe, implemented according to an embodiment. FIG. 14 is an example diagram of the section "E" of the cryoprobe.

In some embodiments, the expansion tubes 5*a* and 5*b* are not directly connected to the supply tube 6. A cooling agent, supplied from supply tube 6, is expelled into a cavity "W" inside the casing 3. The cavity "W" is connected to an inlet opening of the first expansion tube 5*a*, and the second expansion tube 5*b*, according to an embodiment. Thus, according to some embodiments, the cooling agent is expelled into the cavity "W", where increasing pressure causes the cooling agent to flow into the first expansion tube 5*a* and the second expansion tube 5*b*, from which the cooling agent is expelled into the expansion chamber "K".

Figure 15:
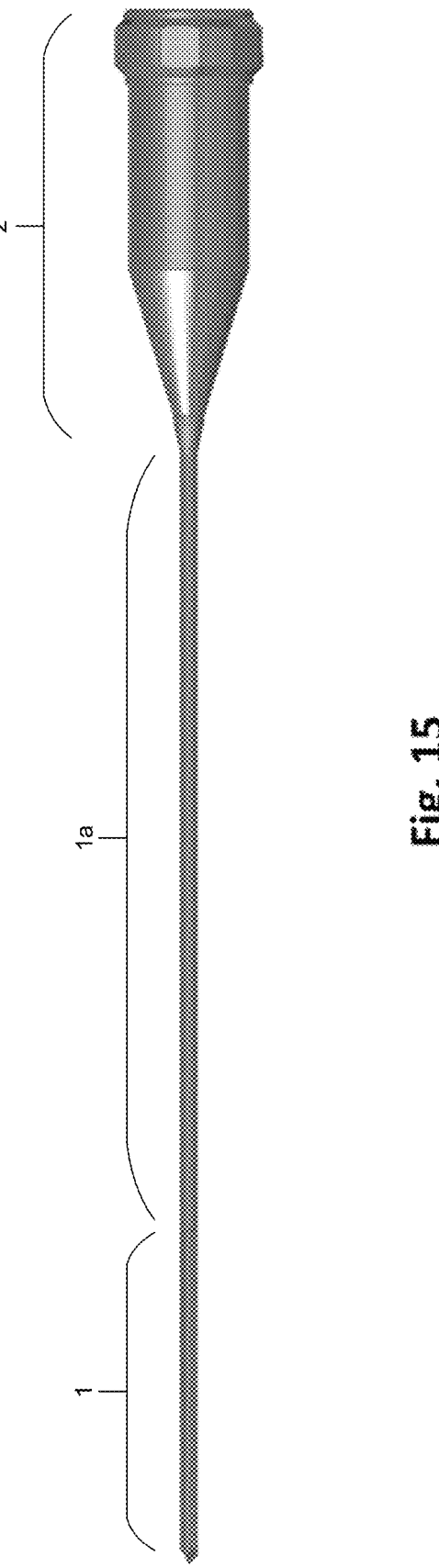
FIG. 15 shows an overview of the probe in a side view with a straight operative part.

FIG. 15 is an example schematic diagram of a side view of a cryoprobe with a straight operative part, implemented in accordance with an embodiment. According to an embodiment, the cryoprobe includes a straight working part 1, which also includes an expansion chamber "K" (not shown here). The working part 1 is connected to a casing 1*a*, which in an embodiment form together the casing 3 discussed above. The casing 1*a* is connected to a handle 2, discussed in more detail above.

Figure 16:
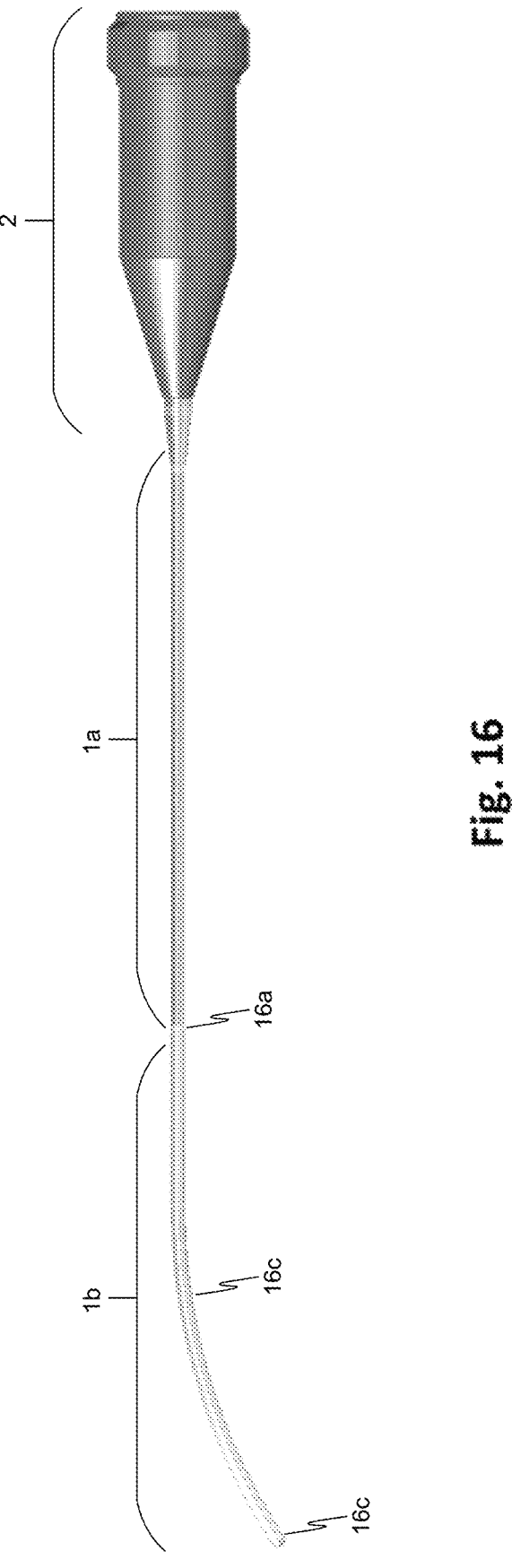
FIG. 16 shows an overview of the probe in a side view with a bent working part.

FIG. 16 is an example schematic diagram of a side view of a cryoprobe with a curved operative part, implemented in accordance with an embodiment. According to an embodiment, the cryoprobe includes a handle 2 connected to a casing 1*a*. The casing 1*a* is connected at a first point 16*a* to a curved working part 1*b*. In an embodiment, the curved working part 1*b* is curved based on the first point 16*a*, a middle point 16*b*, and a tip 16*c*, such that the middle point 16*b* is a point between the first point 16*a* and the tip 16*c*, all located on the working part 1*b*. A curved working part 1*b* is also referred to as having a profile. In an embodiment, a working part 1 (such as discussed in FIG. 7 above), is mechanically bent to a profile.

In some embodiments, a curved working part 1*b* is advantageous, as it allows the cryoprobe to adhere to the sacrum surface. In an embodiment, an electrically isolating coating (such as Teflon®) is applied to the working part 1*b*. For example, the coating is applied, according to an embodiment, up to, and not including, the tip 16*c*. In an embodiment the electrically isolating coating is applied after profiling is achieved.

Figure 17:
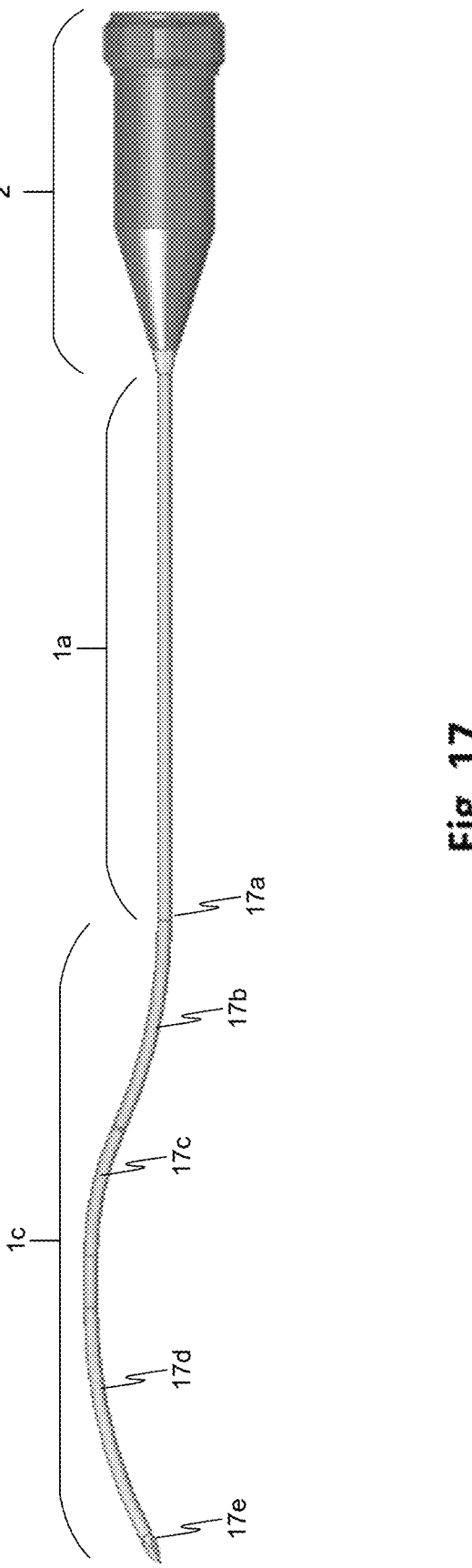
FIG. 17 is an overview of the probe in a side view with a double bent working part.

FIG. 17 is an example schematic diagram of a side view of a cryoprobe with a double curved working part, implemented in accordance with an embodiment. According to an embodiment, the cryoprobe includes a handle 2 connected to a casing 1*a*. The casing 1*a* is connected at a first point 17*a* to a curved working part 1*c*. In an embodiment, the curved working part 1*c* is curved based on the first point 17*a*, a first middle point 17*b*, a second middle point 17*c*, a third middle point 17*d*, and a tip 17*e*, such that the first middle point 17*b* is a point between the first point 17*a* and the second middle point 17*c*, and the third middle point 17*d* is a point between the second middle point 17*c* and the tip 17*e*, all located on the working part 1*c*. According to an embodiment, the first point 17*a*, first middle point 17*b*, and second middle point 17*c* define together a first curve of the curved working part 1*c*. In an embodiment, the second middle point 17*c*, the third middle point 17*d*, and the tip 17*e* define together a second curve of the curved working part 1*c*, such that a concave of the first curve is convex to the second curve.

Figure 18:
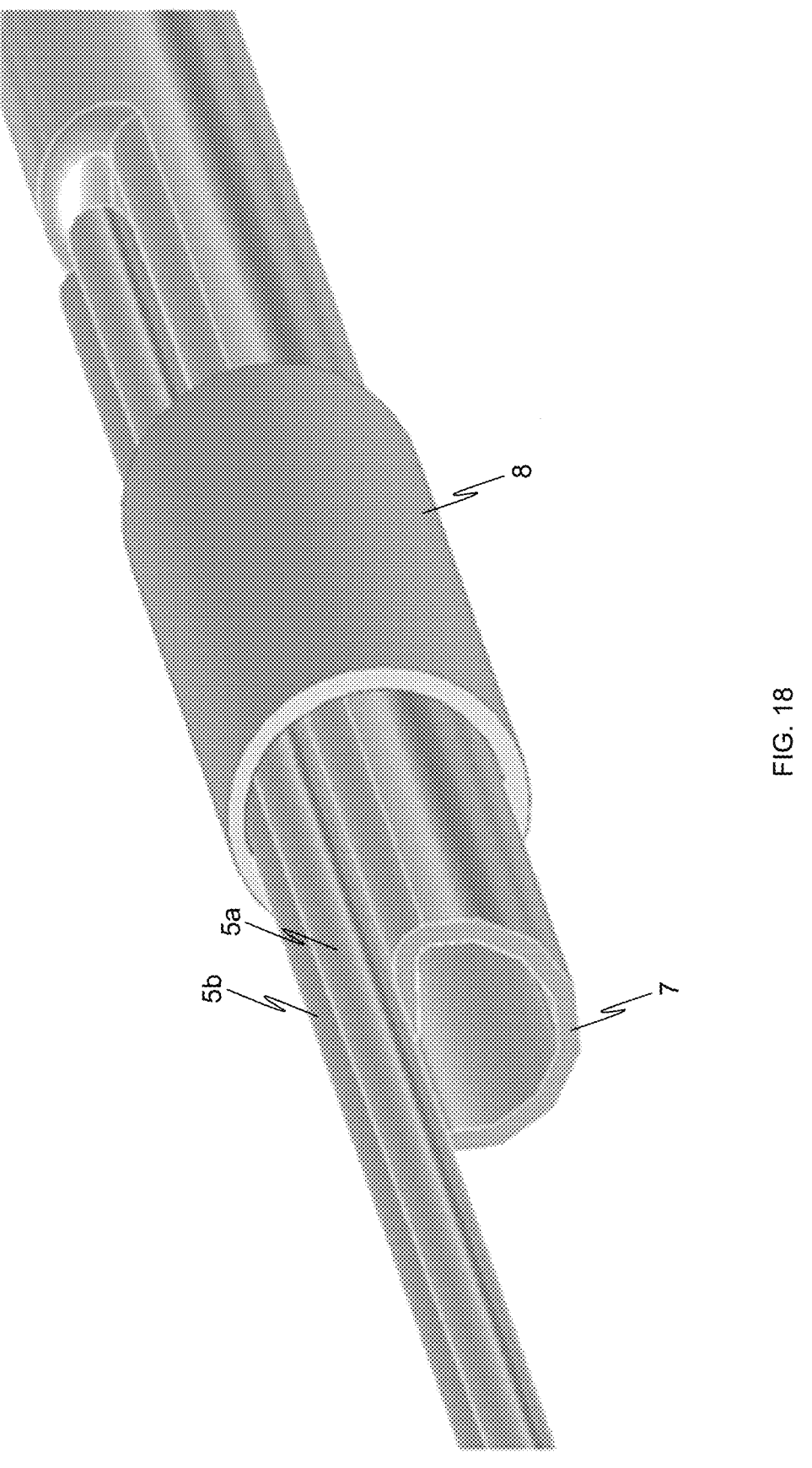
FIG. 18 is an isometric view of a cryoprobe with a sleeve, implemented in accordance with another embodiment.

FIG. 18 is an example schematic diagram of an isometric view of a cryoprobe with a sleeve, implemented in accordance with an embodiment. A first expansion tube 5*a* is position parallel to a second expansion tube 5*b*, according to an embodiment. In certain embodiments, the first expansion tube 5*a* and the second expansion tube 5*b* are positioned above a drain tube 7, which is affixed to the first expansion tube 5*a* and the second expansion tube 5*b* with a sleeve 8.

Figure 19:
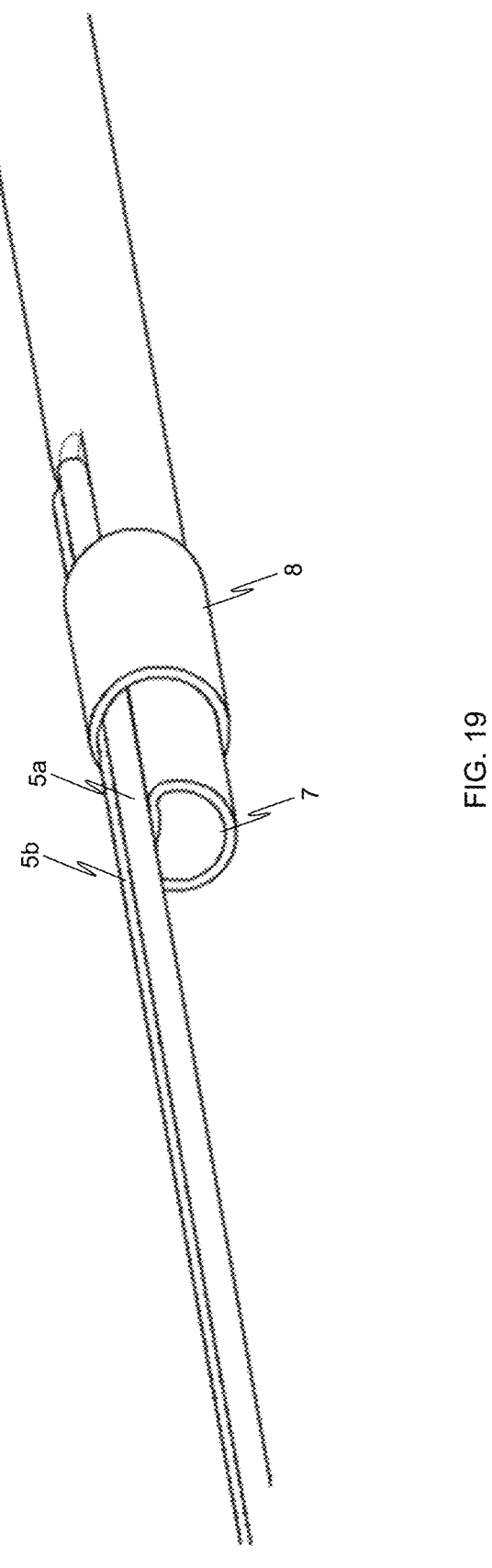
FIG. 19 is an isometric view of a cryoprobe with a sleeve, implemented in accordance with yet another embodiment.

FIG. 19 is an example schematic diagram of another isometric view of a cryoprobe with a sleeve, implemented in accordance with an embodiment. In some embodiments, the first expansion tube 5*a* has a first length, which is longer than a second length of the second expansion tube 5*b*. This is discussed in more detail in FIG. 20 below.

Figure 20:
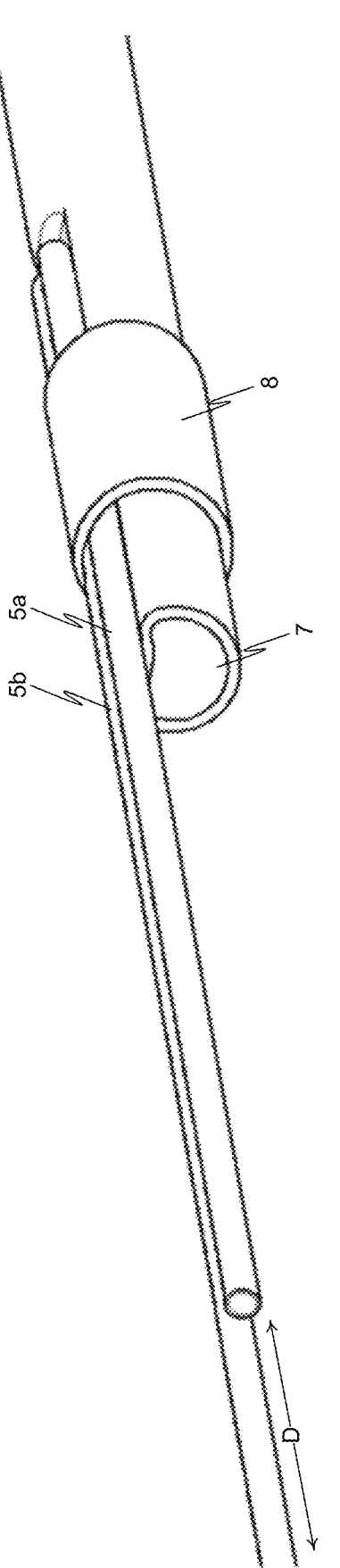
FIG. 20 is an isometric view of a cryoprobe with a sleeve, having a first expansion tube shorter in length than a second expansion tube, implemented in accordance with an embodiment.

FIG. 20 is an example diagram of an isometric view of a cryoprobe with a sleeve, having a first expansion tube shorter in length than a second expansion tube, implemented in accordance with an embodiment. In an embodiment, the first expansion tube 5*a* terminates at an inlet which is position a distance "D" from where the second expansion tube 5*b* terminates at a respective inlet.

Figure 21:
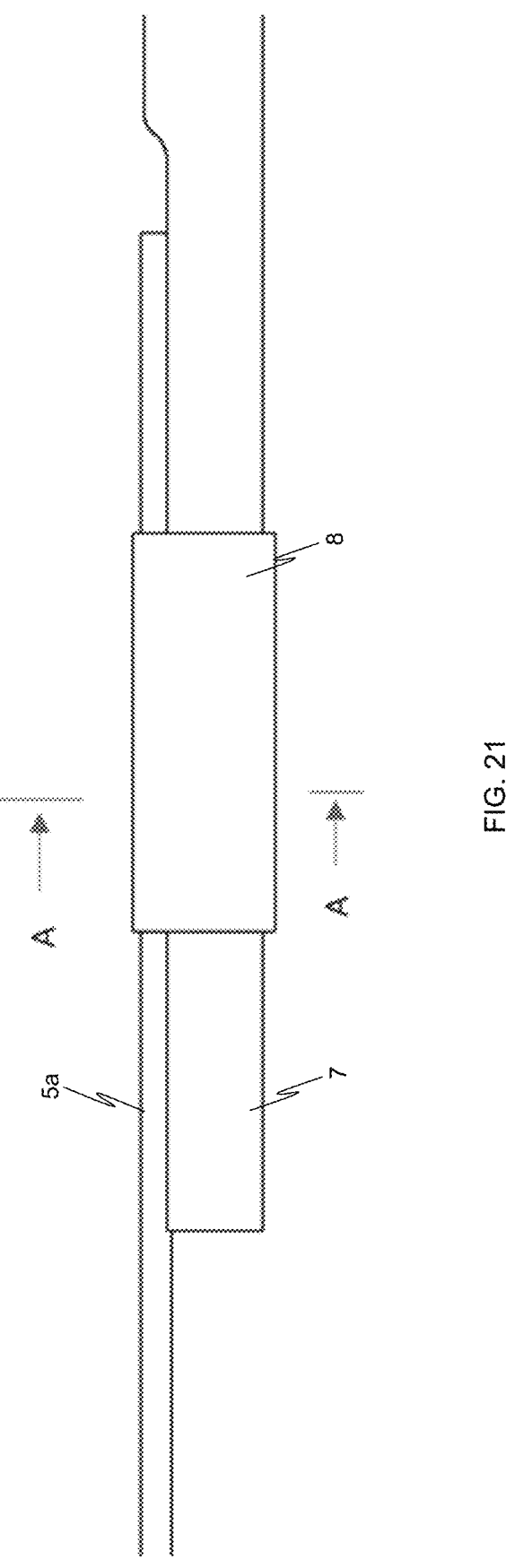
FIG. 21 is a side view of a cryoprobe with a sleeve, implemented in accordance with an embodiment.

FIG. 21 is an example diagram of a side view of a flow assembly of a cryoprobe with a sleeve, implemented in accordance with an embodiment. According to an embodiment, cooling agent "A" flows around the flow assembly as it is drained from the drain tube 7.

Figure 22:
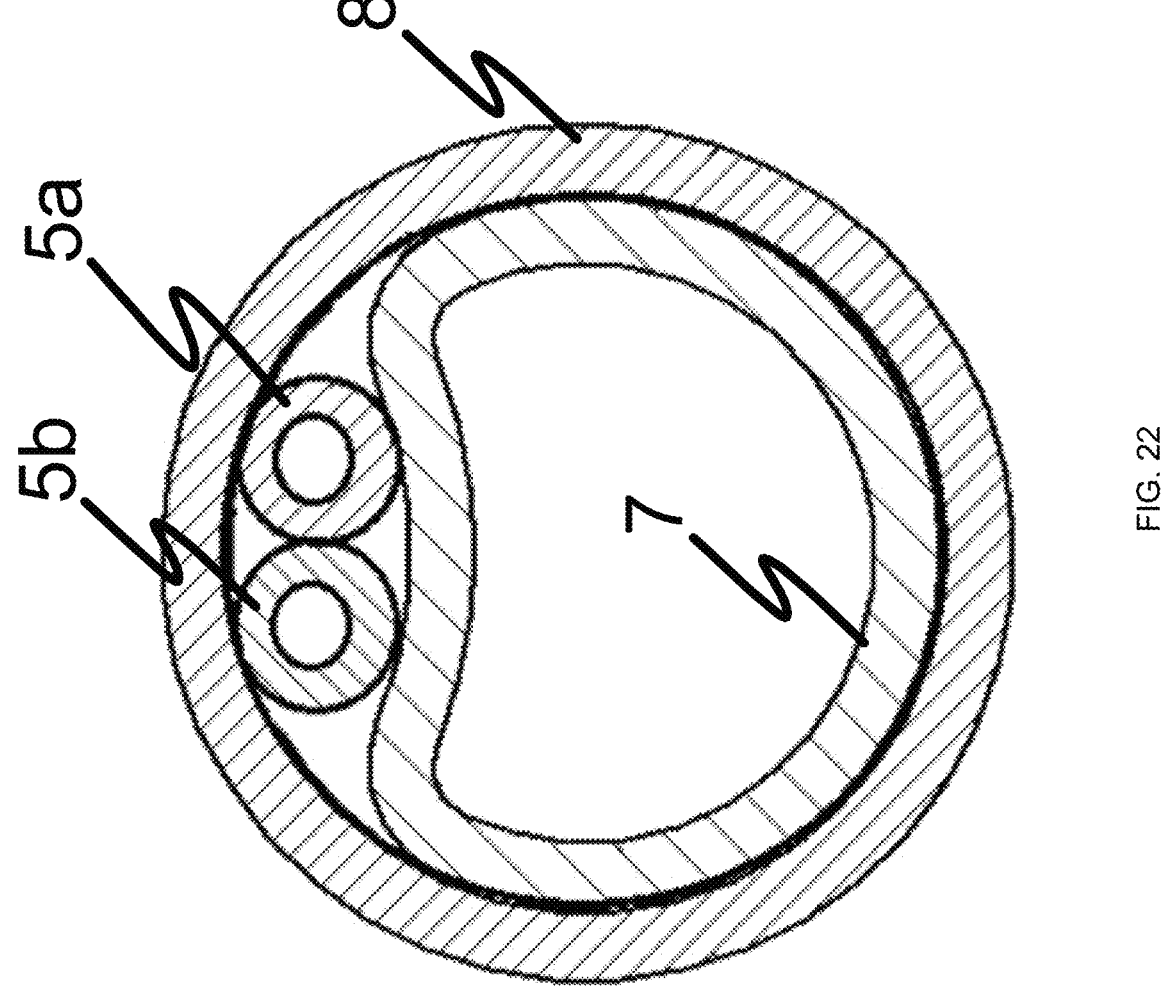
FIG. 22 is a frontal cross section view of a cryoprobe having a first and second expansion tubes, implemented in accordance with an embodiment.

FIG. 22 is an example of a diagram of a frontal cross section view of a cryoprobe having a first and second expansion tubes, implemented in accordance with an embodiment. In an embodiment, the cryoprobe includes a plurality of first expansion tubes 5*a*, a plurality of second expansion tubes 5*b*, a plurality of drain tubes 7, a combination thereof, and the like, all coupled by a sleeve 8, which defines a permitter in which the plurality of expansion tubes, drain tubes, combination thereof, and the like, reside.

Figure 23:
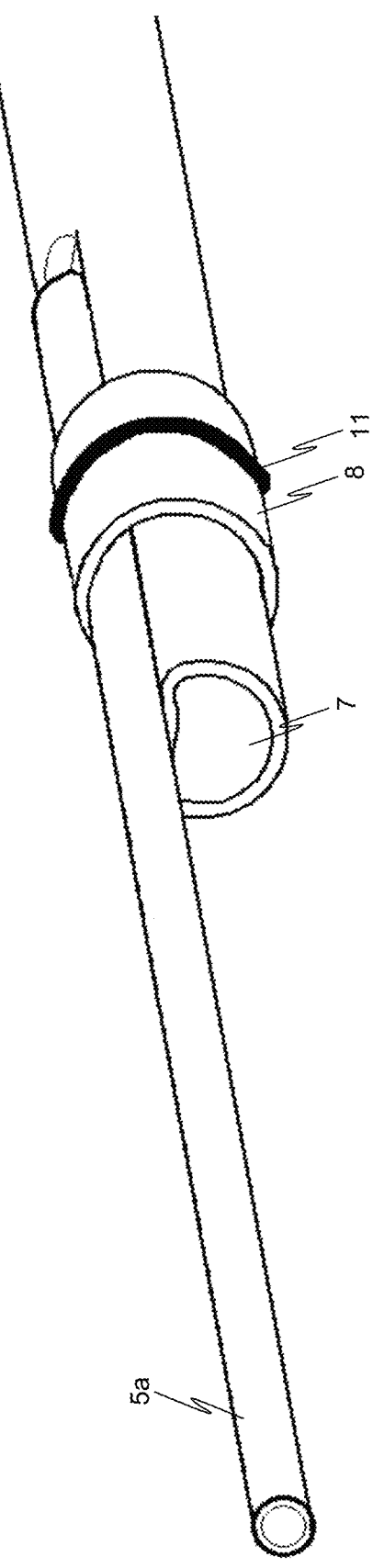
FIG. 23 is a schematic diagram of an isometric view of a cryoprobe with a sleeve and sealer, implemented in accordance with an embodiment.

FIG. 23 is an example schematic diagram of an isometric view of a cryoprobe with a sleeve and sealer, implemented in accordance with an embodiment. In an embodiment, a flow assembly includes a first expansion tube 5*a* and a drain tube 7, at least a section of which is surrounded by a sleeve 8, for example as discussed in more detail above. In an embodiment, a sealer 11, such as an O-ring, is placed on the sleeve, for example on the circumference of the sleeve. This allows to create an efficient seal when placing the sleeve inside a casing of a cryoprobe.

Figure 24:
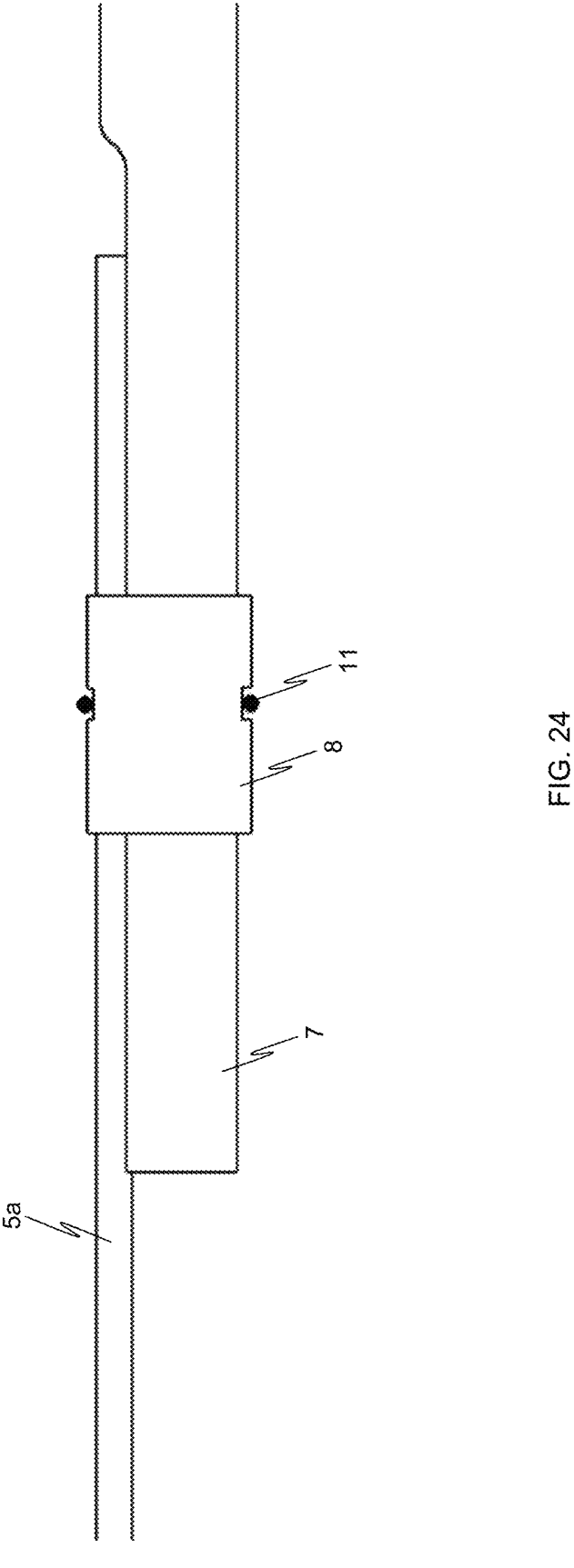
FIG. 24 is a schematic diagram of a side cross-section view of a cryoprobe with a sleeve and sealer, implemented in accordance with an embodiment.

FIG. 24 is an example schematic diagram of a side cross-section view of a cryoprobe with a sleeve and sealer, implemented in accordance with an embodiment. In an embodiment, the sleeve 8 includes an indentation around the sleeve 8, in which a sealer 11, such as an O-ring, is partially placed. This is advantageous as it allows to mechanically affix the sealer in place, and as the indentation increases the contact area with the sealer 11, the effectiveness of the seal is increased.

Figure 25:
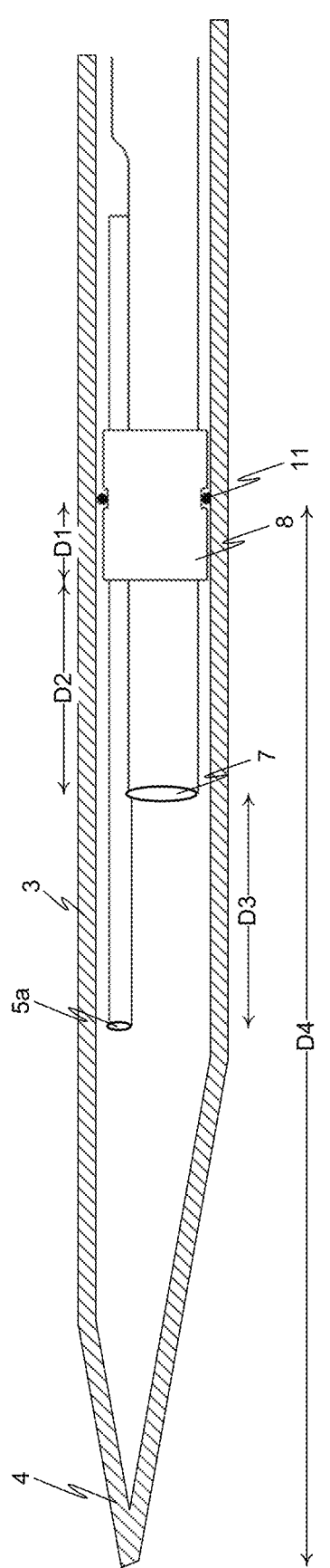
FIG. 25 is a diagram of a side cross-section view of a working part of a cryoprobe, implemented in accordance with an embodiment.

FIG. 25 is an example diagram of a side cross-section view of a working part of a cryoprobe, implemented in accordance with an embodiment. In an embodiment, the cryoprobe includes a sleeve 8 in which a flow assembly is affixed, wherein the sleeve includes an indent in which a sealer 11 is placed. In an embodiment, the sealer is an O-ring of 1.8 by 0.7 mm. In some embodiments, a distance D1 between the indent in which the sealer 11 is placed and a first end of the sleeve 8 is 2 mm. The first end of the sleeve is closer to the tip 4 of the cryoprobe, than a second end of the sleeve 8.

According to an embodiment, a distance D2 between the first end of the sleeve 8 and a drain tube 7 is 3 mm. In an embodiment, a distance D3 between the drain tube 7 and a first expansion tube 5*a* is 10 mm. In some embodiments a total distance D4 between the indent of the sleeve 8 and the tip 4 of the cryoprobe is 25 mm. In some embodiments the above measurement are within −+0.5 mm.

In an embodiment, the surgical cryoprobe is supplied by a carbon dioxide ($CO_2$) cooling agent, a nitrous oxide ($N_2O$) cooling agent, a combination thereof, and the like, which is connected to a flow and temperature control and monitoring unit (not shown).

While this application discusses the treatment application of the sacroiliac joint area, it should be readily appreciated that other cryosurgical procedures are possible utilizing the teachings of the methods and apparatus herein, for example freezing lesions in other parts of the body, such as the prostate, kidneys, and the like, where a tool with a relatively long freezing zone and a small diameter is required to facilitate treatment in a minimally traumatizing insertion.

The surgical cryoprobe according to an embodiment has an external diameter of 2 mm, with a length of 175 mm of the working part 1, capable of generating a uniform and even freezing zone of an equal diameter, along the length of the freezing part, forming the section between the tip of the probe and the sleeve. In an embodiment this section is 40 mm, within a 10% tolerance.

In an embodiment an advantage of the cryoprobe disclosed herein is that by using it, the number of probe insertions relative to treatments performed with a single nerve damaging tool is decreased, therefore reducing patient trauma. Certain disclosed profiles further allow limited maneuvering inside the patient's body, which can cause patient decreased discomfort and avoid damage of healthy tissue.

According to an embodiment the profile of the cryoprobe influences the positioning of the cryoprobe in an anatomical way, therefore it adheres directly to the nerve tissue, without the risk of freezing the skin.

The disclosed solution of the surgical cryoprobe profile is adapted to the anatomical approach to the treated section of the spine, according to an embodiment. A method of treatment using the disclosed cryoprobe includes the probe entering the back of the patient lying in a prone position on a medical bed or other specialized device, with the probe directed along the arch of the distal part of the probe, according to an embodiment. In some embodiments the probe is inserted directly under the skin by making a small incision.

In an embodiment, after contact with the sacrum, a 180° turn must be made to pass the arch of the bone. Then the cryoprobe should be rotated back so that it fits snugly with an arch to the sacrum along sections S1-S4. A freezing zone is created by cooling down to approximately −78° C. (with $CO_2$), −89° C. (with $N_2O$), and the like. In an embodiment the freezing process should last 2 minutes, within a 10% tolerance, followed by defrosting the cryoprobe and re-freezing it. Due to its structure, the cryoprobe defrosts immediately by blocking the cooling agent supply.

Another advantage of the disclosed cryoprobe is that a single surgical cryoprobe is sufficient. In contrast, tools used in chronic pain treatment, operating on the principle of generating high temperature using electricity, require use of additional electrodes (unipolar configuration) or work together with a second probe (bipolar configuration).

Another advantage of low temperature treatment over high temperature treatment generated by electricity is selective and temporary nerve damage (axonotmesis) giving an immediate and long-lasting effect without the risk of neuroma or skin burns and perforation.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A surgical cryoprobe for treating cryolesions in a sacroiliac joint area, comprising:
   at least a first expansion tube having a first length;
   a second expansion tube having a second length, wherein the second length is different than the first length;
   a first supply tube supplying a cooling agent to the first expansion tube;
   a second supply tube simultaneously supplying another cooling agent, which is different than the cooling agent, to the second expansion tube; and
   a drain tube for removing cooling agents from an enclosed working part, wherein the first expansion tube supplies the cooling agent to a first portion of the working part, the second expansion tube supplies the another cooling agent to a second portion of the working part, which is not the first portion of the working part, the working part further including a tip;
   wherein the first expansion tube and the second expansion tube are positioned inside a casing, wherein the first expansion tube, the second expansion tube, and the drain tube are connected to each other by a sleeve, and wherein a sealer positioned on a circumference of the sleeve provides a seal between the sleeve and the casing.

2. The surgical cryoprobe of claim 1, further comprising an expansion chamber defined as a cavity between the tip and the sleeve.

3. The surgical cryoprobe of claim 1, wherein an outlet opening of the first expansion tube is positioned in proximity to the sleeve, and an outlet opening of the second expansion tube is positioned proximate to the tip.

4. The surgical cryoprobe of claim 1, wherein the first expansion tube, the second expansion tube, and the drain tube are together wrapped with an insulating jacket.

5. The surgical cryoprobe of claim 4, wherein the insulating jacket is heat shrinkable.

6. The surgical cryoprobe of claim 1, wherein the first expansion tube, the second expansion tube, and the drain tube are wrapped together with an insulator.

7. The surgical cryoprobe of claim 6, wherein the insulator is any of: a wire, a thread, and a combination thereof.

\*　\*　\*　\*　\*